United States Patent [19]

Feucht

[11] Patent Number: 5,173,104
[45] Date of Patent: Dec. 22, 1992

[54] SELECTIVELY HERBICIDAL METRIBUZIN PLUS BROMOXYNIL

[75] Inventor: Dieter Feucht, Bayerwerk, Fed. Rep. of Germany

[73] Assignee: Bayer Aktiengesellschaft, Leverkusen, Fed. Rep. of Germany

[21] Appl. No.: 592,032

[22] Filed: Oct. 2, 1990

[30] Foreign Application Priority Data

Nov. 10, 1989 [DE] Fed. Rep. of Germany ....... 3937475

[51] Int. Cl.$^5$ .......................................... A01N 43/707
[52] U.S. Cl. .......................................... 71/93; 71/105
[58] Field of Search .................................... 71/93, 105

[56] References Cited

U.S. PATENT DOCUMENTS

| 3,397,054 | 8/1968 | Hart et al. | 71/105 |
| 4,036,632 | 7/1977 | Westphal et al. | 71/93 |
| 4,346,220 | 8/1982 | Fawzi | 71/93 |

FOREIGN PATENT DOCUMENTS 1163109  3/1984  Canada .

OTHER PUBLICATIONS

Weed Control Manual 1991, pp. 4–7, 32–33 & 104–105.
Chemical Abstracts 107: 23/452t. Dec. 21, 1987.
The American Heritage Dictionary, Boston, Houghton Mifflin Company, 1976. p. 296.
Commonwealth Agricultral Bureau, Nr. OWO2-8-00031, Weed Abstracts, Slough et al.: "Annual Weed Control in Wheat and Barley", & Research Journal, Wyoming Agricultural Experiment Station, Nr.119: Research in Weed Science 1977, 1978 S. 14–22.
Commonwealth Agricultural Bureau, Nr. OWO2-9-00640, Weed Abstracts, Slough et al. "Research in Weed Science", & Research Journal, Wyoming Agricultural Experiment Station, Nr. 137,1979, S. 21–32.

*Primary Examiner*—Richard L. Raymond
*Assistant Examiner*—John D. Pak
*Attorney, Agent, or Firm*—Sprung Horn Kramer & Woods

[57] ABSTRACT

A selectively herbicidal composition comprising a selectively herbicidal amount of (1) 4-amino-6-(1,1-dimethylethyl)-3-(methylthio-1,2,4-triazin-5-(4H)-one of the formula

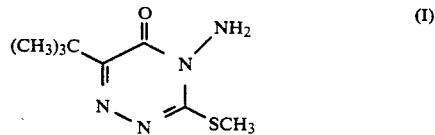

and
(2) 3,5-dibromo-4-hydroxybenzonitrile of the formula

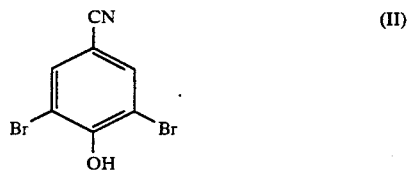

1 Claim, No Drawings

SELECTIVELY HERBICIDAL METRIBUZIN PLUS BROMOXYNIL

The invention relates to novel herbicidal, synergistic active compound combinations composed, on the one hand, of metribuzin and, on the other hand, of bromoxynil and which can be used particularly advantageously for selectively combating weeds in corn crops, it being possible to combat reliably a whole range of important weeds which affect corn.

It has already been disclosed that 4-amino-6- (-1,1-dimethylethyl)-3-(methylthio)-1,2,4-triazin-5(4H)-one (common name: metribuzin) can be used as a selective herbicide in crops such as soy beans, potatoes, wheat, tomatoes, asparagus, lucerne and sugar cane (cf., for example, DE-C-1,542,873 and 1,795,784 and U.S. Pat. Nos. 3,671,523, 3,905,801, 3,961,936, 4,036,632 and 4,346,220). The herbicidal properties of the above compound have been described by, among other authors, W. Draber et al. (Naturwissenschaften, 1968, Vol. 55, p. 446) and L. Eue (Pflanzenschutz-Nachr. (English edition) 1972, Vol. 25, p. 175).

Furthermore, it has already been disclosed that 3,5-dibromo-4-hydroxybenzonitrile (common name: bromoxynil) and also the salts and esters thereof can be used as selective contact herbicides post-emergence in crops such as cereals, corn, sorghum, onions, flax and also newly laid turf (cf., for example, GB-B-1,067,033 and also U.S. Pat. Nos. 3,397,054 and 4,332,613). The herbicidal properties of bromoxynil have been described by, among other authors, R. L. Wain (Nature (London), 1963, Vol. 200, 28) and K. Carpenter and B. J. Heywood (ibid., p. 28). The development of this compound has been discussed by B. J. Heywood (Chem. Ind. (London), 1966, p. 1946).

As a herbicide, metribuzin combats a whole range of dicotyledon and monocotyledon noxious plants in important crops. It acts not only through the soil but also through the leaves by inhibiting photosynthesis in sensitive plants. It has achieved great importance as a herbicide in agriculture.

However, the action of metribuzin on certain weeds is not always adequate. For instance, a certain species of Ipomoea, Ipomoea hederacea, which is of great importance in soy bean and corn growing in North America is not adequately combated using metribuzin application rates which are tolerated by these crops. In particular, the application rates of metribuzin which are tolerated by corn are often unsatisfactory in their breadth of action.

As a herbicide, bromoxynil acts predominantly by contact, so that, after application, newly emerging weeds cannot be dealt with. Moreover, bromoxynil combats only dicotyledon noxious plants, and grass weeds are not combated.

It has now surprisingly been found that the novel active compound combinations composed of (1) 4-Amino-6-(1,1-dimethylethyl)-3-(methylthio)-1,2,4-triazin-5(4H)-one (metribuzin) of the formula (I)

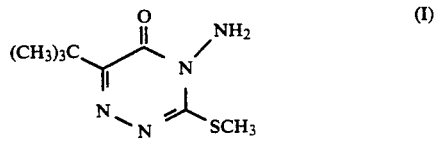

and (2) 3,5-Dibromo-4-hydroxybenzonitrile (bromoxynil) of the formula (II)

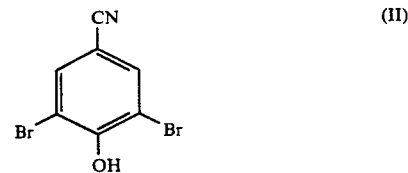

have a particularly high herbicidal efficiency without damaging corn crops.

Surprisingly, the herbicidal efficiency of the active compound combinations according to the invention is significantly higher than the sum of the effects of the individual active compounds. This is therefore a true synergistic effect which could not have been foreseen and is not just a complementary action. The novel active compound combinations are tolerated well in corn crops, the novel active compound combinations also effectively combating weeds such as Ipomoea hederacea and millets which are otherwise difficult to control. The novel active compound combinations are therefore valuable additions to the range of corn herbicides.

Examples of weeds which generally occur as intruders in corn crops and which can be combated using the active compound combinations according to the invention are as follows:

Dicotyledon weeds of the genera: Sinapis, Galium, Stellaria, Matricaria, Anthemis, Galinsoga, Chenopodium, Senecio, Amaranthus, Portulaca, Xanthium, Convolvulus, Ipomoea, Polygonum, Sesbania, Ambrosia, Solanum, Lamium, Veronica, Abutilon, Sida, Datura, Viola, Galeopsis and Centaurea; and Monocotyledon weeds of the genera: Echinochloa, Setaria, Panicum, Digitaria, Phleum, Poa, Festuca, Eleusine, Brachiaria, Lolium, Bromus, Avena, Alopecurus and Apera.

However, the use of the active compound combinations according to the invention is in no way restricted to these genera but also extends in the same manner to other plants.

As already stated, the active compound combinations according to the invention have a powerful action on weeds and grass weeds while being well tolerated by corn crops; particular preference is therefore given to their use as selective corn herbicides.

At certain concentration ratios, the synergistic effect of the active compound combinations according to the invention is particularly highly accentuated. However, the ratios by weight of the active compounds in the active compound combinations can be varied within relatively wide limits. Generally, for every 1 part by weight of active compound of the formula (I) there are 0.1 to 30 parts by weight, preferably 1 to 10 parts by weight and particularly preferably 1 to 8 parts by weight, of the active compound (II).

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound combination, preferably between 0.5 and 90%.

The active compound combinations according to the invention are generally used in the form of finished formulations. However, the active compounds present in the active compound combinations may also be mixed on use into individual formulations, i.e. employed in the form of tank mixes.

Furthermore, the novel active compound combinations, as such or in their formulations, can also be used mixed with other known corn herbicides, finished formulations or tank mixes again being possible. Mixtures with other known active compounds, such as fungicides, insecticides, acaricides, nematicides, bird repellents, growth substances plant nutrients and agents which improve soil structure, are also possible. For certain applications, particularly by the post-emergence method, it can furthermore be advantageous to include, as further additives in the formulations, plant-tolerated mineral or vegetable oils (for example, the commercial preparation "Oleo Dupont 11E") or ammonium salts such as, for example, ammonium sulphate or ammonium rhodanide.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The application rates of the active compound combinations according to the invention can be varied within certain limits; the said application rates depend on, among other factors, the weather and on soil factors. In general, the application rates are between 0.05 and 5 kg per ha, preferably between 0.1 and 1 kg per ha, particularly preferably between 0.2 and 0.6 kg per ha.

The active compound combinations according to the invention may be applied after emergence of the plants, i.e. by the post-emergence method.

The good herbicidal action of the novel active compound combinations can be seen from the examples which follow. While the individual active compounds have inadequacies in their herbicidal action, the combinations have a very effective action on weeds, this action exceeding the simple aggregate of actions.

With herbicides, a synergistic effect is always present if the herbicidal action of the active compound combination is greater than that of the individually applied active compounds.

The action expected from a given combination of two herbicides can be calculated as follows (cf. COLBY, S. R.; "Calculating synergistic and antagonistic responses of herbicide combinations", Weeds 15, pages 20–22, 1967):

If $X = \%$ damage caused by herbicide A at an application rate of p kg/ha and $Y = \%$ damage caused by herbicide B at an application rate of q kg/ha and $E =$ the expected damage from herbicides A and B, at application rates of p and q kg/ha, then $E = X + Y - (X*Y/100)$.

If the actual damage is greater than calculated, the combination has a super-additive action, i.e. it exhibits a synergistic effect.

The examples which follow show that the observed herbicidal action on weeds of the active compound combinations according to the invention is greater than the calculated action, i.e. that the novel active compound combinations have a synergistic action.

Examples

Post-emergence tests

The active compound preparations required for the experiments are prepared by weighing out appropriate amounts of commercially available formulations of metribuzin and bromoxynil and diluting these with water to the desired concentration; different combinations of the two active compounds are prepared by mixing.

The metribuzin formulation used was a 70% strength WG (dispersible granules), (tradename: ®SENCOR, from Bayer AG).

The bromoxynil formulation used was an EC (emulsifiable concentrate) containing 235 g/l of bromoxynil esters (tradename: ®CERTROL B, from Spiess Urania).

The active compound preparations are used to spray test plants 5 to 15 cm in height in such a way that the desired amounts of active compound per unit area are applied in each case. The concentration of the spraying liquors is selected so that, in each case, the desired amounts of active compound are applied in 500 l of water per ha. After being treated, the test plants are kept in a greenhouse under controlled conditions (temperature, air humidity, light) until they are evaluated. After three weeks, the degree of damage to the plants is assessed as % damage in comparison with the development of untreated control plants.

The ratings are as follows:

0 = no action/damage (like the untreated controls)
100 = total destruction

Active compounds, application rates and results can be seen from the tables which follow.

TABLE 1

Post-emergence test/greenhouse

| Active compound or combination | Application rate g/ha (active compound) | Test plants damage or action in % | | | |
|---|---|---|---|---|---|
| | | Corn | | Ipomoea | |
| | | found* | calc.* | found* | calc.* |
| (I) | 60 | 0 | | 0 | |
| -known- | 30 | 0 | | 0 | |
| (II) | 250 | 0 | | 70 | |
| -known- | 125 | 0 | | 60 | |
| | 60 | 0 | | 50 | |
| (I) + (II) | 60 + 250 | 20 | 0 | 90 | 70 |
| according to | 60 + 125 | 0 | 0 | 70 | 60 |
| the invention | 60 + 60 | 0 | 0 | 70 | 50 |
| | 30 + 250 | 10 | 0 | 98 | 70 |
| | 30 + 125 | 0 | 0 | 80 | 60 |
| | 30 + 60 | 0 | 0 | 60 | 50 |

(I) = metribuzin
(II) = bromoxynil
*found = observed damage or action (in percent)
*calc. = calculated damage or action according to the COLBY formula (in percent).

TABLE 2

Post-emergence test/greenhouse

| Active compound or combination | Application rate g/ha (active compound) | Test plants damage or action in % | | | |
|---|---|---|---|---|---|
| | | Corn | | Echinochloa | |
| | | found* | calc.* | found* | calc.* |
| (I) | 60 | 0 | | 40 | |
| -known- | 30 | 0 | | 10 | |
| (II) | 250 | 0 | | 20 | |
| -known- | 125 | 0 | | 10 | |
| | 60 | 0 | | 0 | |
| (I) + (II) | 60 + 250 | 20 | 0 | 98 | 52 |
| according to | 60 + 125 | 0 | 0 | 70 | 46 |
| the invention | 60 + 60 | 0 | 0 | 70 | 40 |
| | 30 + 250 | 10 | 0 | 70 | 28 |
| | 30 + 125 | 0 | 0 | 50 | 20 |
| | 30 + 60 | 0 | 0 | 20 | 10 |

(I) = metribuzin
(II) = bromoxynil
*found = observed damage or action (in percent)
*calc. = calculated damage or action according to the COLBY formula (in percent).

TABLE 3

Post-emergence test/greenhouse

| Active compound or combination | Application rate g/ha (active compound) | Test plants damage or action in % | | | |
|---|---|---|---|---|---|
| | | Corn | | Digitaria | |
| | | found* | calc.* | found* | calc.* |
| (I) | 30 | 0 | | 80 | |
| -known- | | | | | |
| (II) | 250 | 0 | | 10 | |
| -known- | 125 | 0 | | 10 | |
| | 60 | 0 | | 0 | |
| (I) + (II) | 30 + 250 | 10 | 0 | 100 | 72 |
| according to | 30 + 125 | 0 | 0 | 98 | 72 |
| the invention | 60 + 60 | 0 | 0 | 80 | 80 |

(I) = metribuzin
(II) = bromoxynil
*found = observed damage or action (in percent)
*calc. = calculated damage or action according to the COLBY formula (in percent).

TABLE 4

Post-emergence test/greenhouse

| Active compound or combination | Application rate g/ha (active compound) | Test plants damage or action in % | | | |
|---|---|---|---|---|---|
| | | Corn | | Setaria | |
| | | found* | calc.* | found* | calc.* |
| (I) | 30 | 0 | | 30 | |
| -known- | | | | | |
| (II) | 250 | 0 | | 10 | |
| -known- | 125 | 0 | | 0 | |
| | 60 | 0 | | 0 | |
| (I) + (II) | 30 + 250 | 10 | 0 | 70 | 37 |
| according to | 30 + 125 | 0 | 0 | 60 | 30 |
| the invention | 30 + 60 | 0 | 0 | 50 | 30 |

(I) = metribuzin
(II) = bromoxynil
*found = observed damage or action (in percent)
*calc. = calculated damage or action according to the COLBY formula (in percent).

It is understood that the specification and examples are illustrative but not limitative of the present invention and that other embodiments within the spirit and scope of the invention will suggest themselves to those skilled in the art.

I claim:

1. In the growing of corn, the method of selectively combating weeds which comprises, after emergence of the corn, applying to the corn or the locus in which the corn is growing a selectively effective herbicidal amount of a synergistic composition comprising (1) 4-amino-6-(1,1-dimethylethyl)-3-(methylthio)-1,2,4-triazin-5-(4H)-one of the formula $$(CH_3)_3C\underset{N \diagdown N}{\overset{\displaystyle \underset{\displaystyle \|}{O} \diagdown N-NH_2}{\|}}SCH_3 \qquad (I)$$

and
(2) 3,5-dibromo-4-hydroxybenzonitrile of the formula $$\underset{OH}{\underset{Br \diagdown \diagup Br}{\diagup CN}} \qquad (II)$$

wherein the ratio by weight of the active compound of the formula (I) to the active compound of the formula (II) is between about 1:1 and 1:10.

* * * * *